(12) United States Patent
Xu et al.

(10) Patent No.: US 7,057,083 B2
(45) Date of Patent: *Jun. 6, 2006

(54) CATALYST PRETREATMENT WITH C4–C7 OLEFINS IN AN OXYGENATE TO OLEFINS REACTION SYSTEM

(75) Inventors: Teng Xu, Houston, TX (US); Nicolas P. Coute, Houston, TX (US); Kenneth Ray Clem, Humble, TX (US); Keith H. Kuechler, Friendswood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 239 days.

This patent is subject to a terminal disclaimer.

(21) Appl. No.: 10/712,952

(22) Filed: Nov. 12, 2003

(65) Prior Publication Data

US 2005/0101816 A1    May 12, 2005

(51) Int. Cl.
*C07C 1/00* (2006.01)

(52) U.S. Cl. .................. 585/640; 585/639
(58) Field of Classification Search .......... 585/638, 585/639, 634

See application file for complete search history.

(56) References Cited

U.S. PATENT DOCUMENTS

| | | | |
|---|---|---|---|
| 4,677,242 A | 6/1987 | Kaiser | 585/638 |
| 5,817,907 A | 10/1998 | Benazzi et al. | 585/671 |
| 6,046,372 A | 4/2000 | Brown et al. | 585/640 |
| 6,051,746 A | 4/2000 | Sun et al. | 585/639 |
| 6,137,022 A | 10/2000 | Kuechler et al. | 585/638 |
| 6,225,254 B1 | 5/2001 | Janssen et al. | 502/214 |
| 6,436,869 B1 | 8/2002 | Searle et al. | 502/214 |
| 6,437,208 B1 | 8/2002 | Kuechler et al. | 585/640 |
| 6,657,022 B1 * | 12/2003 | Williams et al. | 526/72 |
| 6,734,330 B1 * | 5/2004 | Xu et al. | 585/640 |
| 6,743,747 B1 * | 6/2004 | Xu et al. | 502/214 |

FOREIGN PATENT DOCUMENTS

| | | |
|---|---|---|
| EP | 0 054 375 | 6/1982 |
| WO | WO 01/62382 | 8/2001 |

OTHER PUBLICATIONS

Kolboe, S., "*Methanol Reactions on ZSM-5 and Other Zeolite Catalysts: Autocatalysis and Reaction Mechanism*", Acfa Chem. Scand. A 40 (1986), pp. 711-713.
Kolboe, S., "*On the Mechanism of Hydrocarbon Formation from Methanol Over Protonated Zeolites*", Methane Conversion, Elsevier Science: Amsterdam, (1988), pp. 189-193.
Dahl, I. M. et al., "*On the Reaction Mechanism for Hydrocarbon Formation from Methanol over SAPO-34-1. Isotopic Labeling Studies of the Co-reaction of Ethene and Methanol*", J. Catal. 149 (1994), 749, pp. 458-464.
Dahl, I.M. et al., "*On the Reaction Mechanism for Hydrocarbon Formation from Methanol over SAPO-34-2. Isotopic Labeling Studies of the Co-reaction of Propene and Methanol*", J. Catal. 161 (1996), 161, pp. 304-309.
Song, W.G. et al, "*Methylbenzenes Are the Organic Reaction Centers for Methanol-to-Olefin Catalysis on HSAPO-34*", J. Am. Chem. Soc. (2000), 122, pp. 10726-10727.
Song, W.G. et al, "*Supramolecular Origins of Product Selectivity for Methanol-to-Olefin Catalysis on HSAPO-34*", J. Am. Chem. Soc. (2001), 123, pp. 4749-4754.
Haw, J.F. et al., "*Roles for Cyclopentenyl Cations in the Synthesis of Hydrocarbons from Methanol on Zeolite Catalyst HZSM-5*", J. Am. Chem. Soc. (2000), 122, pp. 4763-4775.
Arstad, B. et al., "*The Reactivity of Molecules Trapped within the SAPO-34 Cavities in the Methanol-to-Hydrocarbons Reaction*", J. Am. Chem. Soc.(2001), 123, pp. 8137-8138.
Xu, T. et al., "*Toward a Systematic Chemistry of Organic Reactions in Zeolites: In Situ NMR Studies of Ketones*", J. Am. Chem. Soc. (1994), 776, pp. 1962-1972.
Song, W.G. et al, "*A Persistent Carbenium Ion on the Methanol-to-Olefin Catalyst HSAPO-34: Acetone Shows the Way*", J. Phys. Chem. B (2001), 105, pp. 4317-4323.

* cited by examiner

Primary Examiner—Walter D. Griffin
Assistant Examiner—In Suk Bullock

(57) ABSTRACT

This invention relates to processes for converting oxygenates to olefins that include a step of pretreating molecular sieve used in the conversion reaction with a $C_4$–$C_7$ olefin composition, which contains one or more $C_4$–$C_7$ olefins. Fresh or regenerated molecular sieve, which is low in carbon content, is contacted or pretreated with the olefin composition to form a hydrocarbon co-catalyst within the pore structure of the molecular sieve, and the pretreated molecular sieve containing the co-catalyst is used to convert oxygenate to a lighter olefin product.

50 Claims, 1 Drawing Sheet

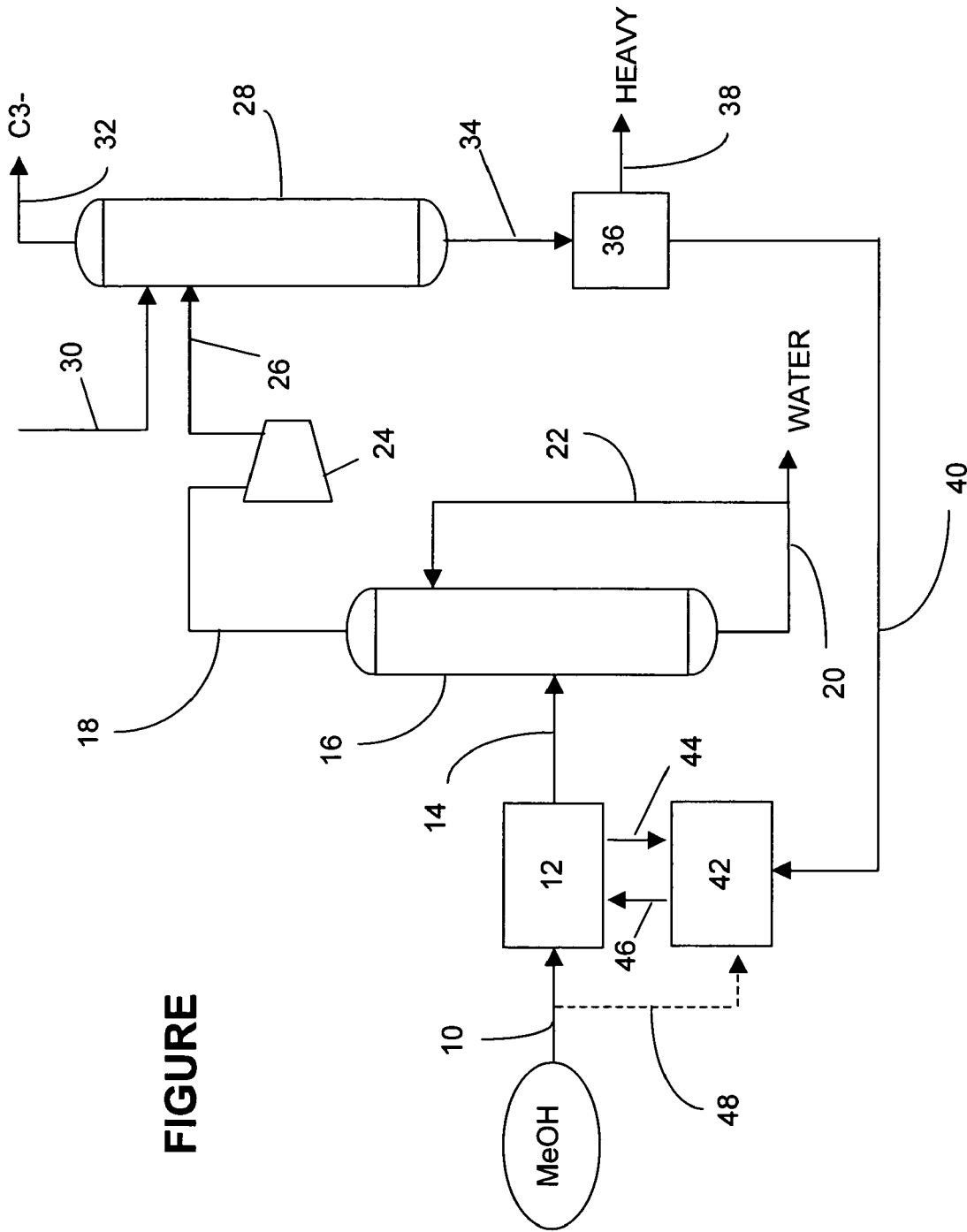
FIGURE

US 7,057,083 B2

CATALYST PRETREATMENT WITH C4–C7 OLEFINS IN AN OXYGENATE TO OLEFINS REACTION SYSTEM

FIELD OF THE INVENTION

This invention relates to processes for converting oxygenates to olefins. In particular, this invention relates to processes for converting oxygenates to olefins that include a step of pretreating catalyst used in the conversion reaction with a $C_4$–$C_7$ olefin composition, which contains one or more $C_4$–$C_7$ olefins.

BACKGROUND OF THE INVENTION

Methanol is used as a feed stock for a variety of chemical manufacturing processes. One process that is more recently being developed is the conversion of methanol to olefin products, particularly products containing the olefins ethylene and propylene. The olefins produced from the methanol conversion process are of suitable quality to be used in polymer manufacturing processes. Of particular commercial concern in the methanol conversion process, however, is whether sufficient quantities of light olefins (i.e., ethylene and propylene) can be produced.

U.S. Pat. No. 4,677,242 (Kaiser) describes the use of a silicoaluminophosphate (SAPO) molecular sieve catalyst for converting various oxygenates, such as methanol, to olefins. According to the patent, the SAPO catalyst is an extremely efficient catalyst for the conversion of oxygenates to light olefin products when the feed is converted in the presence of a diluent. the diluent used has an average kinetic diameter larger than the pores of the SAPO molecular sieve. The selected SAPO molecular sieves have pores that an average kinetic diameter characterized such that the adsorption capacity (as measured by the standard McBain-Bakr gravimetric adsorption method using given adsorbate molecules) shows adsorption of oxygen (average kinetic diameter of about 3.36 angstroms) and negligible adsorption of isobutane (average kinetic diameter of about 5.0 angstroms).

U.S. Pat. No. 6,046,372 (Brown et al.) discloses another method of converting methanol to light olefins. The method incorporates the use of medium pore zeolite molecular sieves, particularly medium pore ZSM type zeolites, in converting methanol and/or dimethyl ether to light olefin. Light olefin production is aided by the use of an aromatic compound as a co-feed. The aromatic compound has a critical diameter less than the pore size of the catalyst, and is capable of alkylation by the methanol and/or dimethyl ether. Ethylene product selectivity is believed to be derived from the back-cracking of ethyl-aromatic intermediates. The formation of the ethyl-aromatic intermediates is believed to be facilitated by a mechanism in which the aromatic compound effectively acts as a catalyst in the conversion of two molecules of methanol to one molecule of ethylene.

U.S. Pat. No. 6,051,746 (Sun et al.) also describes a method for increasing light olefin selectivity in the conversion of oxygenates using a small pore molecular sieve catalyst. The selectivity is increased by exposing a catalyst to a modifier before or during the conversion reaction. The modifier is a polynuclear aromatic having at least three interconnected ring structures, with each ring structure having at least 5 ring members. It is adsorbed onto the catalyst prior to or simultaneously with the introduction of feed.

U.S. Pat. No. 6,137,022 (Kuechler et al.) is to a process for increasing the selectivity of a reaction to convert oxygenates to olefins. The process involves contacting the oxygenate in a reaction zone containing 15 volume percent or less of a catalyst comprising SAPO molecular sieve, and maintaining conversion of the feedstock between 80% and 99% under conditions effective to convert 100% of the feedstock when the reaction zone contains at least 33 volume percent of the molecular sieve material. The process is considered to be beneficial in maximizing the production of ethylene and/or propylene, and to minimize the production of undesired products.

U.S. Pat. No. 6,225,254 (Janssen et al.) is directed to a method of maintaining acid catalyst sites of a SAPO molecular sieve catalyst. According to the patent, catalyst sites are lost when exposed to a moisture-containing environment. In order to maintain the catalyst sites, and thereby preserve catalyst activity, template-containing SAPO molecular sieves are heated in an oxygen depleted environment under conditions effective to provide an integrated catalyst life that is greater than that obtained in a non-oxygen depleted environment.

U.S. Pat. No. 6,436,869 (Searle et al.) is directed to a method of obtaining olefin product high in ethylene and/or propylene content, while reducing the amount of any one or more of $C_1$–$C_4$ paraffin by-products, and to reduce the amount of coke deposits on the catalyst during the reaction. The method is accomplished by providing a catalyst that comprises SAPO crystals, a binder comprising ALPO crystals, and nickel, cobalt and/or iron, wherein the catalyst does not contain significant amounts of amorphous binder, but rather contains crystalline SLPO.

U.S. Pat. No. 6,437,208 (Kuechler et al.) discloses a method for making olefin product from an oxygenate-containing feedstock. In the method, a SAPO molecular sieve catalyst is contacted with the oxygenate-containing feedstock in a reactor at an average catalyst feedstock exposure index of at least 1.0. The average catalyst feedstock exposure index is the total weight of oxygenate plus hydrocarbon fed to the reactor divided by the total weight of fresh and regenerated SAPO molecular sieve (i.e., excluding binder, inerts, etc., of the catalyst composition) sent to the reactor, both total weights measured over the same period of time. The method is shown to be effective in maintaining a high ethylene and propylene selectivity.

WO 01/62382 A2 (ExxonMobil Chemical Patents Inc.) discloses that selectivity to ethylene and propylene can be increased by pretreating a SAPO molecular sieve to form an integrated hydrocarbon co-catalyst within the framework of the molecular sieve prior to contacting with oxygenate feed. Acetone, methanol, propene, butene, pentene and hexene are given as examples of pretreatment compounds capable of forming an integrated hydrocarbon co-catalyst. The conditions for pretreatment include pretreating at a lower temperature relative to the reaction temperature. A preferred pretreatment vessel is an auxiliary fluidized bed reactor system associated with the oxygenate conversion reactor.

In spite of the recent technological advances in converting oxygenates to olefins, there remains a need to further increase the quantity of light olefins in the conversion product. In particular, there remains a need to increase product selectivity to ethylene and propylene, and particularly to ethylene. There also remains a need to reduce the amount of undesirable by-products in converting the oxygenates to olefins.

SUMMARY OF THE INVENTION

This invention provides processes for converting oxygenates to olefins that show enhanced selectivity to ethylene and/or propylene. The processes involve pretreating the conversion catalyst with a $C_4$–$C_7$ olefin composition in a pretreatment zone.

In one aspect, the invention provides a process for making an olefin product from an oxygenate feed. The process includes a step of contacting a metalloaluminophosphate molecular sieve having a porous framework structure with a $C_4$–$C_7$ olefin composition in a pretreatment zone to form an integrated hydrocarbon co-catalyst within the porous framework. The metalloaluminophosphate molecular sieve containing the integrated hydrocarbon co-catalyst is then contacted with an oxygenate in an oxygenate conversion zone to convert the oxygenate to olefin product. Preferably, the pretreatment zone is at a temperature the same as or higher than that of the reaction zone.

In another aspect of the invention, there is provided a process for making an olefin product and polyolefin from an oxygenate feed. The process includes a step of contacting a silicoaluminophosphate molecular sieve with a $C_4$–$C_7$ olefin composition to form an integrated hydrocarbon co-catalyst within the porous framework. The silicoaluminophosphate molecular sieve containing the integrated hydrocarbon co-catalyst is the with an oxygenate to convert the oxygenate to olefin product, and at least one olefin in the olefin product is contacted with a polyolefin forming catalyst to form polyolefin.

In one embodiment, the pretreatment zone is at a temperature higher than that of the reaction zone. Preferably, the pretreatment zone is at a temperature of at least 10° C. higher, more preferably at least 20° C. higher, and most preferably at a temperature of at least 50° C. higher than that of the reaction zone.

In another embodiment, the molecular sieve contacting the olefin composition in a pretreatment zone has a carbon content of not greater than 2 wt %, based on total weight of the molecular sieve, prior to contact with the olefin. Preferably, the molecular sieve contacting the olefin composition in a pretreatment zone has a carbon content of not greater than 1.5 wt %, more preferably not greater than 1 wt %, and most preferably not greater than 0.5 wt %, based on total weight of the molecular sieve, prior to contact with the olefin.

In yet another embodiment of the invention, the molecular sieve containing the integrated hydrocarbon co-catalyst in the oxygenate removal zone has a hydrocarbon content of at least 0.1 wt %, based on total weight of the molecular sieve, prior to contacting the oxygenate. Preferably, the molecular sieve containing the integrated hydrocarbon co-catalyst in the oxygenate removal zone has a hydrocarbon content of at least 1 wt %, more preferably at least 5 wt %, based on total weight of the molecular sieve, prior to contacting the oxygenate.

In another embodiment, the molecular sieve contacts the olefin composition in the pretreatment zone at a WHSV that is lower than that at which the molecular sieve contacts the oxygenate. Preferably, the molecular sieve contacts the olefin composition in the pretreatment zone at WHSV that is at least 5 hr$^{-1}$ lower, more preferably at least 10 hr$^{-1}$ lower, and most preferably at least 15 hr$^{-1}$ lower, than that at which the molecular sieve of step b) contacts the oxygenate.

In an alternative embodiment, the molecular sieve contacts the olefin composition in the pretreatment zone at an olefin to molecular sieve weight ratio of from 0.1:1 to 5:1. Preferably, the molecular sieve contacts the olefin composition in the pretreatment zone at an olefin to molecular sieve weight ratio of from 0.5:1 to 3:1, more preferably from 1:1 to 2:1.

Desirably, the metalloaluminophosphate molecular sieve is silicoaluminophosphate molecular sieve. Preferably, the metalloaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, metal containing molecular sieves thereof, and combinations thereof.

The olefin composition contains sufficient olefin to pretreat the molecular sieve. Preferably, the olefin composition contacting the molecular sieve in the pretreatment zone comprises at least 5 wt % olefin, based on total weight of the composition. In one embodiment, the olefin composition contacting the molecular sieve in the pretreatment zone comprises from 5 wt % to 75 wt % olefin, based on total weight of the composition. Preferably, a majority of the olefin is butene. Desirably, the contact of the molecular sieve with the oxygenate in the oxygenate conversion zone converts at least 90 wt % of the oxygenate to olefin product.

BRIEF DESCRIPTION OF THE DRAWING

One example of the various embodiments of this invention is shown in the attached FIGURE, wherein the FIGURE is a flow diagram of a process of converting methanol to olefin product, and a portion of the olefin in the product is separated and used to pretreat fresh or regenerated molecular sieve catalyst contacting the methanol.

DETAILED DESCRIPTION OF THE INVENTION

I. Pretreatment of Molecular Sieve with Olefin

This invention is directed to processes for making olefin product from an oxygenate feed. The processes include a step of pretreating a fresh or regenerated metalloaluminophosphate molecular sieve, which is low in carbon content, with an olefin. The olefin forms a hydrocarbon co-catalyst within the pore structure of the molecular sieve, and the pretreated molecular sieve containing the co-catalyst is used to convert oxygenate to a lighter olefin product (i.e., ethylene or propylene, or mixture thereof).

At relatively higher pretreatment temperatures, heavier olefins such as butene, pentene, hexene, and heptene are effective at providing molecular sieve catalyst materials that have increased selectivity to forming ethylene and/or propylene in oxygenate to olefin reaction processes. This means that the olefin compounds can be used to pretreat a molecular sieve catalyst (i.e., form a co-catalyst within the molecular sieve) at a relatively high temperature such that subsequent contact of the pretreated molecular sieve with oxygenate will convert a significant amount of the oxygenate directly to ethylene and propylene. The resulting olefin product, will, therefore, contain a significant amount of ethylene and propylene, with relatively low amounts of undesired by-products.

II. Types of Molecular Sieves

The molecular sieves that are included in the catalyst or catalyst mixtures used in the conversion of oxygenates to olefins in this invention are preferably metalloaluminophosphate molecular sieves that have a molecular framework that include [AlO$_4$] and [PO$_4$] tetrahedral units, such as metal containing aluminophosphates (AlPO). In one embodiment, the metalloaluminophosphate molecular sieves include [AlO$_4$], [PO$_4$] and [SiO$_4$] tetrahedral units, such as silicoaluminophosphates (SAPO).

Various silicon, aluminum, and phosphorus based molecular sieves and metal-containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO4), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference. Other molecular sieves include those described in R. Szostak, Handbook of Molecular Sieves, Van Nostrand Reinhold, New York, N.Y. (1992), which is herein fully incorporated by reference.

The more preferred molecular sieves are SAPO molecular sieves, and metal-substituted SAPO molecular sieves. Suitable metal substituents are alkali metals of Group IA of the Periodic Table of Elements, an alkaline earth metals of Group IIA of the Periodic Table of Elements, a rare earth metals of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, transition metals of Groups IVB, VB, VIIB, VIIB, VIIIB, and IB of the Periodic Table of Elements and mixtures of any of these metal species. In one embodiment, the metal is selected from the group consisting of Co, Cr, Cu, Fe, Ga, Ge, Mg, Mn, Ni, Sn, Ti, Zn and Zr, and mixtures thereof. The metal atoms may be inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the metalloaluminophosphate molecular sieve is represented, on an anhydrous basis, by the formula:

$$mR:(M_xAl_yP_z)O_2$$

wherein R represents at least one templating agent, preferably an organic templating agent; m is the number of moles of R per mole of (M$_x$Al$_y$P$_z$)O$_2$ and m has a value from 0 to 1, preferably 0 to 0.5, and most preferably from 0 to 0.3; x, y, and z represent the mole fraction of Al, P and M as tetrahedral oxides, where M is a metal selected from the group consisting of Group IA, IIA, IB, IIIB, IVB, VB, VIIB, VIIB, VIIIB and Lanthanide's of the Periodic Table of Elements. Preferably M is one or more metals selected from the group consisting of Si, Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

In one embodiment of the invention, the metalloaluminophosphate molecular sieves are silicoaluminophosphate molecular sieves, containing silicon and aluminum. Desirably, the metalloaluminophosphate molecular sieves of this invention are silicoaluminophosphate molecular sieves that contain Si and Al, at a Si/Al ratio of not greater than about 0.5, preferably not greater than about 0.3, more preferably not greater than about 0.2, still more preferably not greater than about 0.15, and most preferably not greater than about 0.1. In another embodiment, the Si/Al ratio is sufficiently high to allow for increased catalytic activity of the molecular sieve. Preferably, the metalloaluminophosphate molecular sieves are silicoaluminophosphate molecular sieves that contain Si and Al at a ratio of at least about 0.005, more preferably at least about 0.01, and most preferably at least about 0.02.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18, AlPO-34 and metal containing derivatives thereof, such as one or a combination of SAPO-18, SAPO-34, AlPO-34, AlPO-18, and metal containing derivatives thereof, and especially one or a combination of SAPO-34, AlPO-18, and metal containing derivatives thereof.

In an embodiment, the molecular sieve is an intergrowth material having two or more distinct crystalline phases within one molecular sieve composition. In particular, intergrowth molecular sieves are described in U.S. Patent Application Publication No. 2002-0165089 and International Publication No. WO 98/15496, published Apr. 16, 1998, both of which are herein fully incorporated by reference. For example, SAPO-18, AlPO-18 and RUW-18 have an AEI framework-type, and SAPO-34 has a CHA framework-type. Thus, the molecular sieve used herein may comprise at least one intergrowth phase of AEI and CHA framework-types, especially where the ratio of CHA framework-type to AEI framework-type, as determined by the DIFFaX method disclosed in U.S. Patent Application Publication No. 2002-0165089, is greater than 1:1.

Various methods for synthesizing molecular sieves or modifying molecular sieves are described in U.S. Pat. No. 5,879,655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. Patent Application Publication No. 20020055433 published May 9, 2002 (cooling molecular sieve), U.S. Pat. No. 6,448,197 (metal impregnation including copper), U.S. Pat. No. 6,521,562 (conductive microfilter), and U.S. Patent Application Publication No. 20020115897 published Aug. 22, 2002 (freeze drying the molecular sieve), which are all herein fully incorporated by reference.

In general, molecular sieve catalyst is also referred to as formulated molecular sieve catalyst. The formulated catalyst optionally contains binder and matrix materials. Conventionally, formulated catalyst is made by mixing together molecular sieve crystals (which includes template) and a liquid, optionally with matrix material and/or binder, to form a slurry. The slurry is then dried (i.e., liquid is removed), without completely removing the template from the molecular sieve. Since this dried molecular sieve catalyst includes template, it has not been activated, and is considered a preformed catalyst. However, the preformed catalyst must be activated before use, and this invention provides appropriate methods to protect the activated catalyst from significant deactivation.

The liquid used to form the slurry can be any liquid conventionally used in formulating molecular sieve catalysts. Non-limiting examples of suitable liquids include water, alcohol, ketones, aldehydes, esters, or a combination thereof. Water is a preferred liquid.

Matrix materials are optionally included in the slurry used to make the formulated molecular sieve catalyst of this invention. Such materials are typically effective as thermal sinks assisting in shielding heat from the catalyst composition, for example, during regeneration. They can further act to densify the catalyst composition, increase catalyst strength such as crush strength and attrition resistance, and to control the rate of conversion in a particular process. Non-limiting examples of matrix materials include one or more of: rare earth metals, metal oxides including titania, zirconia, magnesia, thoria, beryllia, quartz, silica or sols, and mixtures thereof, for example, silica-magnesia, silica-zirconia, silica-titania, silica-alumina and silica-alumina-thoria.

In one embodiment, matrix materials are natural clays, such as those from the families of montmorillonite and kaolin. These natural clays include kaolins known as, for example, Dixie, McNamee, Georgia and Florida clays. Non-limiting examples of other matrix materials include: halloysite, kaolinite, dickite, nacrite, or anauxite. Optionally, the matrix material, preferably any of the clays, are calcined, acid treated, and/or chemical treated before being used as a slurry component. Under the optional calcination treatment, the matrix material will still be considered virgin material as long as the material has not been previously used in a catalyst formulation.

In a particular embodiment, the matrix material is a clay or a clay-type composition, preferably a clay or clay-type composition having a low iron or titania content, and most preferably the matrix material is kaolin. Kaolin has been found to form a pumpable, high solid content slurry; it has a low fresh surface area, and it packs together easily due to its platelet structure.

Binders are also optionally included in the slurry used to make the formulated molecular sieve catalysts of this invention. Such materials act like glue, binding together the molecular sieve crystals and other materials, to form a formulated catalyst composition. Non-limiting examples of binders include various types of inorganic oxide sols such as hydrated aluminas, silicas, and/or other inorganic oxide sols. In one embodiment of the invention, the binder is an alumina-containing sol, preferably aluminium chlorohydrate. Upon calcining, the inorganic oxide sol, is converted into an inorganic oxide matrix component, which is particularly effective in forming a hardened molecular sieve catalyst composition. For example, an alumina sol will convert to an aluminium oxide matrix following heat treatment.

The molecular sieve crystals are mixed with liquid, and the optional matrix material and/or binder, using conventional techniques to form a slurry. The components can be mixed in any order, and the mixture is thoroughly stirred to form the slurry. The more thorough the stirring, the better the consistency of the slurry.

Liquid is removed from the slurry containing the molecular sieve crystals to form a preformed molecular sieve catalyst. Preferably, the slurry is fed to a forming unit that produces the preformed molecular sieve catalyst composition. The forming unit may be any conventional unit, such as a spray dryer, pelletizer, extruder, etc. In a preferred embodiment, the forming unit is spray dryer, which removes water from the slurry by a heating or drying process. Preferably, the forming unit is maintained at a temperature sufficient to remove a majority of the liquid from the slurry.

The molecular sieve material is activated by removing the template from the preformed molecular sieve catalyst composition so as to expose the active catalytic sites to the environment. The template can be removed by any conventional technique, including for example by elution methods or by heating such as calcining. The molecular sieve crystals themselves can be activated for immediate catalytic use or for storing or transporting prior to use. However, it is preferred that the molecular sieves be formulated into a preformed catalyst, then activated by calcining. The formulated product generally provides the most effective particle size and hardness for commercial scale equipment.

III. Olefin Pretreatment Composition

The olefin that is used to pretreat the molecular sieve composition is an olefin compound, preferably other than ethylene or propylene, that has a kinetic diameter less than the average pore opening of the molecular sieve. Desirably, the olefin is one or more $C_4$–$C_7$ olefins. The olefin is preferably selected from the group consisting of butene, pentene, hexene, heptene, or any combination thereof.

The olefin is contacted with the molecular sieve so as to form an integrated hydrocarbon co-catalyst within the pore structure of the molecular sieve. The integrated hydrocarbon co-catalyst is preferably a single ring aromatic compound. More preferably, the integrated hydrocarbon co-catalyst is a benzene-based compound. Still more preferably, the integrated hydrocarbon co-catalyst is identified by Solid State Nuclear Magnetic Resonance (SSNMR) spectra comprising a peak in the 18 ppm to 40 ppm region and a peak in the 120 ppm to 150 ppm region. Alternatively, the intensity of the peak in the 18 ppm to 40 ppm region is negligible, with a single peak near 128 ppm. In one embodiment, the molecular sieve exhibits a ratio in the intentisty of the peak in the 18 ppm to 40 ppm region to the intensity of the peak in the 120 ppm to 150 ppm region of not greater than about 1.0. More preferably, the molecular sieve exhibits a ratio in the intentisty of the peak in the 18 ppm to 40 ppm region to the intensity of the peak in the 120 ppm to 150 ppm region of between about 0.15 and 0.7.

An important advantage of using the olefin compositions of this invention to pretreat the molecular sieve is that, at higher pretreatment temperatures, the olefins are particularly advantageous in forming the co-catalyst compound within the molecular sieve. A fresh or regenerated molecular sieve containing co-catalyst is in its most desirable state for converting oxygenates to ethylene and propylene.

Another advantage in using the olefin compositions of this invention as pretreatment agents is that this provides a way to reduce undesirable by-products in the overall conversion of oxygenates to olefins. Typically, heavier olefins such as the $C_4$–$C_7$ olefins are considered as undesirable by-products, because the value of those olefins are considerably lower than ethylene and propylene. Therefore, the by-products of the oxygenate to olefins reaction process can be used to enhance selectivity of the catalyst to provide the more desirable ethylene and propylene products.

Enough olefin is used to pretreat fresh or regenerated molecular sieve to form the active co-catalyst. Typically, the amount of olefin used to pretreat the molecular sieve is greater than other compounds that can also be used as pretreatment agents such as, for example, acetaldehyde. However, there is substantially enough olefin by-product produced in the oxygenate to olefin reaction process that most if not all of the olefin by-product produced can be used as a pretreatment agent. In cases where the oxygenate to olefin reaction process is particularly efficient at converting oxygenate to ethylene and propylene, and relatively low amounts of olefin by-products are formed, various oxygenate components, particularly acetaldehyde, can be added to the olefin pretreatment composition and the composition containing the combined components used to effectively form the co-catalyst.

The olefin pretreatment composition provides a substantial increase in the amount of ethylene and propylene in the oxygenate to olefin reaction process. Typically, an effective amount of olefin as a pretreatment agent will result in an increase of at least 2 wt % ethylene and propylene in the olefin product. Preferably, the amount of olefin applied as a pretreatment agent will result in an increase of at least 3 wt % ethylene and propylene in the olefin product, more preferably at least 4 wt % ethylene and propylene in the olefin product.

In one embodiment, the molecular sieve that is to be pretreated contacts the olefin composition in a pretreatment zone at an olefin to molecular sieve weight ratio of from 0.1:1 to 5:1. This ratio is based on total amount of olefin compounds in the composition, and on total weight of molecular sieve, excluding any other non-molecular sieve components that may be present in a formulated molecular sieve composition, including matrix, binder, etc. Preferably, the molecular sieve that is to be pretreated contacts the olefin composition at an olefin to molecular sieve weight ratio of from 0.5:1 to 3:1, more preferably from 1:1 to 2:1.

The advantages of using olefin compounds as a pretreatment composition are readily achieved in compositions containing a majority of the $C_4$–$C_7$ olefin compounds produced in the oxygenate to olefin reaction process, particularly a majority of the $C_4$–$C_6$ olefin compounds produced in the oxygenate to olefin reaction process. In a preferred embodiment, the pretreatment composition contains a majority of the $C_4$–$C_5$ olefin compounds produced in the oxygenate to olefin reaction process, particularly a majority of the $C_4$ olefin compounds produced in the oxygenate to olefin reaction process.

The olefin pretreatment compounds of this invention are obtained, in one embodiment, from an oxygenate to olefin product stream. Such olefins are considered by-products in the oxygenate to olefins reaction process, and are removed from the product stream using any conventional means capable of removing such by-products to the appropriate level. Conventional distillation techniques are particularly desirable methods, and temperatures and pressures effective for separating the by-product olefins from the ethylene and propylene containing product according to boiling point are used to separate the compounds.

In order to obtain a particularly high degree of separation between the heavier olefins and any entrained oxygenated hydrocarbons from ethylene and/or propylene, absorption or extractive distillation can be optionally used. Extractive distillation differs from conventional distillation to the extent that the ethylene and propylene are distilled from the heavier olefins and any entrained oxygenated hydrocarbons using an extractant to aid the distillation process. Absorption differs from the extractive distillation in that an extractant is used to aid in the separation, but no additional heat is added to the system as in distillation.

Absorption and extractive distillation are carried out using a vessel or tower having internal packing or trays that creates a temperature difference from top to bottom of the tower. The upper portion of the tower is the cooler portion, and higher volatile components in the feed exit from the top of the tower.

An extractant or solvent is added to the extractive distillation vessel or tower or the absorber so as to enhance or suppress the volatility of the heavier olefins, or oxygenated hydrocarbons that can also be present, relative to the ethylene and propylene. This makes it easier to separate the heavier olefins and oxygenated hydrocarbons from the ethylene and propylene.

Absorbents or extractants which can be used in this invention are preferably liquids at 1 atm. These extractants are preferably oxygenated hydrocarbon compounds that act as solvents or absorbents for the $C_4$–$C_7$ olefin compounds, or as solvents or extractants for the oxygenated hydrocarbons present. Preferably, the extractants have an average boiling point at 1 atm of not greater than 120° C., more particularly not greater than 110° C., and most particularly not greater than 100° C. Average boiling point, as defined herein, takes into account the boiling point of each compound in the absorbent on a weight average basis. For example, an absorbent containing 90 wt. % of a compound having a boiling point of 100 degrees and 10 wt. % of a compound having a boiling point of 200 degrees would have an average boiling point of 110 degrees.

The extractants are also desirably polar compositions effective at removing oxygenated hydrocarbons that are also effective as pretreatment agents. Such compositions preferably contain compounds such as water, monohydric alcohols, polyhydric alcohols, or mixtures thereof. Preferred monohydric alcohols include methanol, ethanol and propanol. Preferred polyhydric alcohols include glycols. Preferred glycols include ethylene glycol and tri-ethylene glycol. It is desirable that the absorbent contain at least about 75 wt. % monohydric alcohol and/or polyhydric alcohol, preferably at least about 85 wt. %, more preferably at least about 90 wt. %, and most preferably at least about 95 wt. %. Methanol is most preferred as the absorbent in this invention.

The extractive distillation process is particularly effective for not only separating heavier olefins from the lighter olefins, ethylene and propylene, but also in removing very low concentrations of oxygenate hydrocarbons present in an olefin stream. In one embodiment of the invention, extractant is added at an upper region of an extractive distillation column, and the olefin containing oxygenated hydrocarbon, particularly acetaldehyde, is added at a side region of the column. Separated ethylene and/or propylene is recovered from the column in a first fraction, preferably from an upper portion of the column, and the separated heavier olefins and oxygenated hydrocarbons, particularly acetaldehyde, is recovered in a second fraction, preferably from a lower portion of the column. A majority of the added extractant (i.e., at least 50% of the amount added to the column) is also recovered from a lower portion of the column, preferably along with the recovered heavier olefin and oxygenated hydrocarbon.

In one embodiment of the invention, the separated $C_4$–$C_7$ olefin stream comprises at least a majority (i.e., at least 50%) of the $C_4$–$C_7$ olefins present in the provided olefin stream. Preferably, the separated $C_4$–$C_7$ olefin stream comprises at least about 75%, more preferably at least about 90%, of the $C_4$–$C_7$ olefin compounds present in the provided olefin stream.

Preferably, the separated $C_4$–$C_7$ olefin stream comprises at least about 5 wt % olefin compounds, based on total weight of the separated olefin stream. More preferably, the separated $C_4$–$C_7$ olefin stream comprises at least about 10 wt % olefin compounds, most preferably about 15 wt % olefin compounds, based on the total weight of the separated stream. The separated $C_4$–$C_7$ containing stream preferably includes acetaldehyde. In one embodiment, the stream comprises at least about 1,000 wppm acetaldehyde; in another, at least about 2,000 wppm; and in yet another, at least about 5,000 wppm, based on the total weight of the stream.

In another embodiment of the invention, the stream containing the separated $C_4$–$C_7$ product includes extractant. In one embodiment, the stream comprises at least about 50 wt % extractant, in another at least about 60 wt %, and yet another at least about 70 wt %. Preferably the extractant is methanol.

Other examples of oxygenated hydrocarbons which can be used as extractants, or mixed with the $C_4$–$C_7$ olefin stream and used as a pretreatment component, include include those having a boiling point at 1 atm of from about 50° C. to about 90° C. Preferred examples of such hydrocarbons include methanol, acetone, and methyl ethyl ketone.

In one embodiment, the $C_4$–$C_7$ olefin containing stream that is used as the pretreatment stream comprises from about 5 wt % to about 75 wt % of one or more $C_4$–$C_7$ olefins, based on total weight of the pretreatment stream. Preferably, the pretreatment stream comprises from about 7.5 wt % to about 65 wt % of one or more $C_4$–$C_7$ olefins, more preferably from about 10 wt % to about 55 wt % of one or more $C_4$–$C_7$ olefins, based on total weight of the pretreatment stream.

In another embodiment of the invention, $C_8$ and higher olefins are removed from the separated $C_4$–$C_7$ olefin composition prior to contact of the olefin composition with the molecular sieve in the pretreatment zone. Preferably, the $C_4$–$C_7$ olefin composition that is separated from the olefin product of the oxygenate conversion reaction is sent to a distillation process and the components in the $C_4$–$C_7$ olefin composition having a boiling point about equal to or greater than that of heptene are substantially removed, particularly about equal to or greater than that of heptene-2. According to this embodiment, a step of separating compounds having a boiling point of about equal to or greater than that of heptene from the $C_4$–$C_7$ olefin composition, prior to pretreatment, is optionally included as part of the invention.

IV. Pretreatment Conditions

According to the invention, fresh, regenerated, or a combination of fresh and regenerated molecular sieve is pretreated with the olefin composition in a pretreatment zone to form an integrated hydrocarbon co-catalyst within the porous framework of the molecular sieve. Effective pretreatment of the molecular sieve is obtained over a wide range of temperatures, pressures and space velocities. In general, the pretreatment temperature (i.e., the temperature in the pretreatment zone) is at least about the same as or greater than the oxygenate reaction temperature (i.e., the temperature in the oxygenate reaction zone). Preferably, the pretreatment temperature is greater than the oxygenate reaction temperature. Desirably, the temperature in the pretreatment zone is at least 10° C. higher than that in the oxygenate reaction zone. Preferably, the temperature in the pretreatment zone is at least 25° C., more preferably at least 50° C., and most preferably at least about 100° C. higher than that in the reaction zone.

In one embodiment, the temperature in the pretreatment zone is at least 450° C. Preferably, the temperature in the pretreatment zone is at least 500° C., and most preferably at least 550° C.

In another embodiment, the temperature in the pretreatment zone is from about 150° C. to about 750° C. Preferably, the temperature in the pretreatment zone is from about 200° C. to about 750° C., more preferably from about 250° C. to about 750° C.

Pretreatment of the molecular sieve is particularly effective on fresh, activated catalyst, or regenerated catalyst. Such catalyst is substantially low in total carbon content. As the fresh or regenerated catalyst contacts the olefin pretreatment composition, the integrated hydrocarbon co-catalyst forms within the internal pore structure of the molecular sieve. In one embodiment, the molecular sieve that contacts the olefin pretreatment composition to form the integrated hydrocarbon co-catalyst has a total carbon content of not greater than about 2 wt % prior to contact with the olefin pretreatment composition. Preferably the molecular sieve catalyst that contacts the olefin pretreatment composition has a total carbon content of not greater than about 1.5 wt %, more preferably not greater than about 1 wt %, and most preferably not greater than about 0.5 wt %, prior to contact with the olefin pretreatment composition.

Following pretreatment, the molecular sieve contains the integrated hydrocarbon co-catalyst, which is a benzene type compound, within the various cages of the internal pore structure. In addition to using SSNMR to determine appropriate pretreatment of the molecular sieve, an additional embodiment involves measuring hydrocarbon content of the molecular sieve that has contacted the olefin pretreatment composition. In one embodiment, the molecular sieve containing the integrated hydrocarbon co-catalyst has a hydrocarbon content of at least 0.1 wt %, preferably at least 1 wt %, more preferably at least about 5 wt %, and most preferably at least about 10 wt %, based on total weight of the molecular sieve, which excludes non-molecular sieve components such as binder, matrix, etc., which are optionally present in a catalyst composition.

In general, the molecular sieve that is being pretreated contacts the olefin composition in the pretreatment zone at a weight hourly space velocity (WHSV) that is lower than the WHSV of the molecular sieve contacting the oxygenate in the oxygenate reaction zone. In one embodiment, the molecular sieve contacts the olefin composition at a WHSV that is at least 5 hr$^{-1}$ lower than that of the molecular sieve contacting the oxygenate in the oxygenate reaction zone. Preferably, the molecular sieve contacts the olefin composition at a WHSV that is at least about 10 hr$^{-1}$, more preferably at least about 15 hr$^{-1}$ lower than that of the molecular sieve contacting the oxygenate in the oxygenate reaction zone.

In one embodiment, the molecular sieve and the olefin pretreatment composition contact one another in a pretreatment zone at a WHSV of from about 5 hr$^{-1}$ to about 200 hr$^{-1}$. WHSVs in the lower range are preferred, particularly from about 10 hr$^{-1}$ to about 100 hr$^{1}$, and more particularly from about 10 hr$^{-1}$ to about 50 hr$^{-1}$.

The pretreatment zone can be contained in a separate pretreatment zone or within a reactor vessel where the catalytic conversion of oxygenate to olefin takes place. In one embodiment, a separate pretreatment vessel is used. In a particular embodiment, the pretreatment vessel is an auxiliary fluidized bed reactor associated with the oxygenate conversion reactor and regenerator system. The auxiliary reactor is capable of continuously receiving catalyst from the regenerator and subsequently supplying pretreated catalyst to the oxygenate conversion reactor.

In another embodiment, pretreatment is carried out within the same vessel where the catalytic conversion of oxygenate to olefin product takes place. Preferably, two separate temperature zones are maintained to get proper introduction of hydrocarbon and formation of the integrated hydrocarbon co-catalyst. In one aspect, the molecular sieve to be pretreated is introduced into one zone along with the olefin pretreatment composition to form the integrated hydrocarbon co-catalyst. Then, the pretreated molecular sieve containing the integrated hydrocarbon co-catalyst is sent to the other zone and contacted with oxygenate to convert the oxygenate to olefin product. Operating conditions in the two zones are controlled for pretreatment and oxygenate reaction conditions. Either zone or both zones optionally includes heating or cooling equipment such as heat exchangers, steam coils, and cooling coils. In one embodiment, the pretreatment zone includes cooling equipment.

V. Converting Oxygenate to Olefins Using Pretreated Molecular Sieve

The molecular sieve pretreated with the olefin composition of this invention is contacted with oxygenate feedstock and the oxygenate is converted to olefin product. In a preferred embodiment of the process of the invention, the oxygenate feedstock contains one or more oxygenates, more specifically, one or more organic compound(s) containing at least one oxygen atom. In the most preferred embodiment of the process of this invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

Using the catalyst composition of the invention for the conversion of a feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example greater than 75 weight percent, and preferably greater than 78 weight percent. Typically, the amount ethylene produced in weight percent based on the total weight of hydrocarbon product produced, is greater than 30 weight percent, such as greater than 35 weight percent, for example greater than 40 weight percent. In addition, the amount of propylene produced in weight percent based on the total weight of hydrocarbon product produced is greater than 20 weight percent, such as greater than 25 weight percent, for example greater than 30 weight percent, and preferably greater than 35 weight percent.

In a preferred embodiment of the invention, at least 85% of the oxygenate in the oxygenate feedstream, is converted to olefin product. Preferably at least 90%, more preferably at least 95%, and most preferably at least 98% of the oxygenate in the oxygenate feedstream, is converted to olefin product.

In addition to the oxygenate component, such as methanol, the feedstock may contain one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

The olefin conversion process can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the olefin conversion process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

In the olefin conversion process, the weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 $hr^{-1}$ to about 3000 $hr^{-1}$, example from about 5 $hr^{-1}$ to about 1500 $hr^{-1}$, and conveniently from about 10 $hr^{-1}$ to about 1000 $hr^{-1}$. In one embodiment, the WHSV is greater than 20 $hr^{-1}$ and, where feedstock contains methanol and/or dimethyl ether, is in the range of from about 20 $hr^{-1}$ to about 300 $hr^{-1}$.

Where the olefin conversion process is conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec. See for example U.S. Pat. No. 6,552,240, the contents of which is fully incorporated herein by reference.

The olefin conversion process of the invention can be conducted as a fixed bed process. Preferably, the olefin conversion process is carried out as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one practical embodiment, the process is conducted as a fluidized bed process or high velocity fluidized bed process utilizing a reactor system, a regeneration system and a recovery system.

In the olefin conversion process, the reactor system preferably includes a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment this invention, regenerated or fresh, uncoked catalyst, prior to being introduced to the riser reactor(s), is pretreated with the olefin composition of this invention, and then contacted with oxygenate feedstock to convert the oxygenate to olefin product at high selectivity to ethylene and propylene.

In another embodiment, oxygenate feedstock is fed to the olefin conversion reactor as a liquid and/or a vapor in a range of from 0.1 weight percent to about 99.9 weight percent, such as from about 1 weight percent to about 99 weight percent, more typically from about 5 weight percent to about 95 weight percent, based on the total weight of the feedstock including any diluent contained therein. The liquid and vapor feedstocks may be the same composition, or may contain varying proportions of the same or different feedstocks with the same or different diluents.

The feedstock entering the reactor system is preferably converted, partially or fully, in the first reactor zone into a gaseous effluent that enters the disengaging vessel along with the coked catalyst composition. In the preferred embodiment, cyclone(s) are provided within the disengaging vessel to separate the coked catalyst composition from the gaseous effluent containing one or more olefin(s) within the disengaging vessel. Although cyclones are preferred, gravity effects within the disengaging vessel can also be used to separate the catalyst composition from the gaseous effluent. Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172 kPaa) to about 150 psia (1034 kPaa), and conveniently from about 30 psia (207 kPaa) to about 60 psia (414 kPaa).

The residence time of the catalyst composition in the regenerator may be in the range of from about one minute to several hours, such as from about one minute to 100 minutes. The amount of oxygen in the regeneration flue gas (i.e., gas which leaves the regenerator) may be in the range of from about 0.01 mole percent to about 5 mole percent based on the total volume of the gas. The amount of oxygen in the gas used to regenerate the coked catalyst (i.e., fresh or feed gas) is typically at least about 15 mole percent, preferably at least about 20 mole percent, and more preferably from about 20 mole percent to about 30 mole percent, based on total amount of regeneration gas fed to the regenerator.

The burning of coke in the regeneration step is an exothermic reaction, and in an embodiment, the temperature within the regeneration system is controlled by various techniques in the art including feeding a cooled gas to the regenerator vessel. The catalyst is not cooled too much, however, since it is preferred to pretreat the regenerated catalyst with the olefin pretreatment composition at higher temperatures.

In one embodiment of the invention, the regenerated catalyst composition is withdrawn from the regeneration system and combined with a fresh molecular sieve catalyst composition and/or re-circulated molecular sieve catalyst composition and/or feedstock and/or fresh gas or liquids, and returned to the riser reactor(s). A carrier, such as an inert gas, feedstock vapor, steam or the like, may be used, semi-continuously or continuously, to facilitate the introduction of the regenerated catalyst composition to the reactor system, preferably to the one or more riser reactor(s). The regenerated catalyst is preferably pretreated with the olefin composition of this invention prior to combining with any unregenerated catalyst that is re-circulated from the reactor.

By controlling the flow of the regenerated catalyst composition that is being pretreated and the flow of any re-circulated and unregenerated catalyst that is to be combined with the pretreated catalyst composition, the optimum carbon content on the combined molecular sieve catalyst composition entering the reactor is maintained. Conventional techniques for controlling the flow of a catalyst composition described in Michael Louge, *Experimental Techniques, Circulating Fluidized Beds*, Grace, Avidan and Knowlton, eds., Blackie, 1997 (336–337), which is herein incorporated by reference.

Carbon or coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

Gaseous effluent is withdrawn from the disengaging system and is passed through a recovery system to recover product and by-products, including the olefin pretreatment composition of this invention. Conventional recovery systems, techniques and sequences can be used in separating olefin(s) and purifying olefin(s) from the gaseous effluent. Conventional recovery systems generally comprise one or more or a combination of various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment, for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a dethanizer, a depropanizer, a wash tower often referred to as a caustic wash tower and/or quench tower, absorbers, adsorbers, membranes, ethylene (C2=) splitter, propylene (C3=) splitter and butene (C4=) splitter.

Various recovery systems useful for recovering olefin(s), such as ethylene, propylene and/or butene, are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which are herein incorporated by reference.

Typically, in converting one or more oxygenates to olefin(s) having 2 or 3 carbon atoms, a minor amount hydrocarbons, particularly olefin(s), having 4 or more carbon atoms is also produced. The amount of $C_4+$ olefins is normally less than 20 weight percent, such as less than 10 weight percent, for example less than 5 weight percent, and particularly less than 2 weight percent, based on the total weight of the effluent gas withdrawn from the process, excluding water. Typically, therefore the recovery system may include one or more reaction systems for converting the $C_4+$ olefins to useful products.

Non-limiting examples of such reaction systems are described in U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4 and C5 Olefinic Streams*, Pet. & Coal, Vol. 37, No. 4 (1995) (dimerizing or oligomerizing propylene, butylene and pentylene), which are all fully herein incorporated by reference.

The preferred light olefin(s) produced by any one of the processes described above are high purity ethylene and propylene products that contain the individual ethylene and propylene compounds in an amount greater than 80 percent, such as greater than 90 weight percent, such as greater than 95 weight percent, for example at least about 99 weight percent, based on the total weight of the product.

In one practical embodiment, the olefin forming process of the invention is integrated with one or more polyolefin processes to produce any one of a variety of polyolefins. (See, for example, U.S. patent application Ser. No. 09/615,376 filed Jul. 13, 2000, which is herein fully incorporated by reference.) In such an integrated process, at least one olefin in the olefin product stream, preferably ethylene or propylene, is separated and contacted with a polymerization catalyst to form a polyolefin product (e.g., polyethylene or polypropylene). The polyolefin product can be further treated as desired or shipped to other destinations for further treatment or processing.

Polymerization processes that can be integrated with the olefin conversion processes of this invention include solution, gas phase, slurry phase, high pressure processes, and combinations thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above. However, the preferred polymerization catalysts are the Ziegler-Natta, Phillips-type, metallocene, metallocene-type and advanced polymerization catalysts, and mixtures thereof.

In a preferred embodiment, the integrated process comprises a process for polymerizing one or more olefin(s) in the presence of a polymerization catalyst system in a polymerization reactor to produce one or more polymer products, wherein the one or more olefin(s) have been made by converting an alcohol, particularly methanol, using a molecular sieve catalyst composition as described above. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

VI. Example of Recovering an Olefin Pretreatment Stream

One embodiment of the invention is shown in the FIGURE. According to the embodiment in the FIGURE, methanol is sent through a line 10 to a reaction zone, which includes molecular sieve catalyst for converting the methanol to light olefin product. In the reaction zone, the methanol contacts the molecular sieve, which contains an integrated hydrocarbon co-catalyst, and forms the olefin product. The olefin products exits the reaction zone 12 through a line 14 and enters a quench tower 16. The quench tower 16 separates water formed in the reaction zone from the olefin product. The olefin product leaves the quench tower 16 through an overhead line 18, and the water leaves the quench tower 16 through a line 20. A portion of the water in the line 20 is sent back to the quench tower 16 through a line 22 to further aid in separating the water from the olefin product.

The olefin product flows through the line 18 to a compressor 24, and exits the compressor 24 by way of a line 26.

From the line 26, olefin product enters into a separator 28, which separates lighter olefin compounds from the heavier olefin compounds. To further aid in the separation, particularly to further aid in removing oxygenated hydrocarbons which can also be entrained in the olefin product, an extractant is used. The extractant is sent to the separator 28 through a line 30. The ligher olefins (e.g., propylene and lighter boiling point olefins) are removed from the separator 28 through an overhead line 32, and the heavier olefins (e.g., butenes and heavier boiling point olefins) are removed through a bottoms line 34. The heavier olefins are sent to a second separator 36 for further separation.

In the separator 36, heavy compounds such as octene and heavier olefins, including some of the oxygenated hydrocarbons, are separated from the remaining olefins. The heavy compounds are removed through a line 38 and the remaining compounds are removed through a line 40.

The remaining compounds that are sent through the line 40 are used as a pretreatment agent, which can include at least a portion of the extractant. The pretreatment agent is sent to a pretreatment zone 42 and is contacted with fresh or regenerated molecular sieve. Regenerated molecular sieve is sent to the pretreatment zone 42 by way of a line 44 from the reaction zone 12. The reaction zone 12, in this embodiment, includes a regenerator that removes carbon material from the molecular sieve. This molecular sieve is sent through the line 44, and contacts the olefin pretreatment agent in the pretreatment zone 42 to form a molecular sieve containing the integrated hydrocarbon co-catalyst. The molecular sieve containing the integrated hydrocarbon co-catalyst is then sent through a line 46 to contact the methanol feed. On occasions when there is insufficient quantity of olefin pretreatment agent to effectively treat the molecular sieve, a portion of the methanol is sent through line 48 and added to the pretreatment zone 42 as a part of the pretreatment agent.

vii. Examples of Pretreated Sieve

EXAMPLE 1

A mixture of 95 mg of formulated SAPO-34 catalyst and 1 g of 100-μm silicon carbide was loaded into a microflow reactor made of ¼" silicon steel tubing and equipped with a vaporizer for vaporizing the feed to the reactor. The reactor temperature was increased to 550° C. while the catalyst was under helium flow (24 ml/min), and held for ca. 30 to 40 minutes for the temperature to stabilize.

The catalyst was pretreated by flowing 1.87 g 1-butene per gram of molecular sieve in the formulated catalyst through the reactor at 25 psig and at a WHSV of 56 $hr^{-1}$. After the flow of 1-butene was stopped, 48 ml/min of helium was flowed through the reactor while the temperature was reduced to 475° C. The flow was continued for about 45 minutes.

Methanol was then injected at 25 psig, 475° C. and at a WHSV of 100 $hr^{-1}$. Effluent was collected using a 16-loop Valco valve. The effluent was analyzed using an on-line gas chromatograph (Hewlett Packard 6890) equipped with a flame ionization detector and a Q-column. The results are shown in Table 1. $C_1$, $C_2=$, $C_2°$, $C_3=$, $C_3°$, $C_4s$, $C_5+s$, and $C_{2+3}=$ in the ethylene, ethane, propene, propane, butenes and butanes, hydrocarbons that contain five or more than five carbons, and ethylene plus propene, respectively.

EXAMPLE 2

The procedure of Example 1 was repeated, except that the catalyst was pretreated by flowing the 1-butene through the reactor at a WHSV of 28 hr$^{-1}$. The results are shown in Table 1.

EXAMPLE 3

The procedure of Example 1 was repeated, except that the catalyst was pretreated by flowing the 1-butene through the reactor at a WHSV of 14 hr$^{-1}$. The results are shown in Table 1.

EXAMPLE 4

The procedure of Example 1 was repeated, except that the catalyst was pretreated by flowing the 1-butene through the reactor at a WHSV of 7 hr$^{-1}$. The results are shown in Table 1.

TABLE 1

| WHSV (hr$^{-1}$) | $C_1$ | $C_2=$ | $C_2°$ | $C_3=$ | $C_3°$ | $C_4s$ | $C_5+s$ | $C_{2+3}=$ | Lifetime (g/g sieve) | $C_2=/C_3=$ |
|---|---|---|---|---|---|---|---|---|---|---|
| 56 | 2.39 | 41.32 | 0.30 | 39.61 | 0.36 | 11.38 | 4.64 | 80.93 | 12.20 | 1.04 |
| 28 | 3.55 | 43.27 | 0.32 | 38.72 | 0.29 | 10.27 | 3.57 | 81.99 | 10.05 | 1.12 |
| 14 | 3.50 | 44.18 | 0.32 | 38.89 | 0.28 | 9.81 | 3.03 | 83.07 | 6.00 | 1.14 |
| 7 | 4.22 | 48.61 | 0.34 | 37.25 | 0.25 | 6.98 | 2.35 | 85.86 | 2.34 | 1.30 |

EXAMPLE 5

Example 2 was repeated except that the SAPO-34 catalyst was pretreated with 1-butene at 350° C. Following pretreatment, the temperature of the reactor was raised to 475° C., and methanol injected as in Example 2. The results are shown in Table 2.

TABLE 2

| WHSV (hr$^{-1}$) | $C_1$ | $C_2=$ | $C_2°$ | $C_3=$ | $C_3°$ | $C_4s$ | $C_5+s$ | $C_{2+3}=$ | Lifetime (g/g sieve) | $C_2=/C_3=$ |
|---|---|---|---|---|---|---|---|---|---|---|
| 28 | 1.81 | 38.81 | 0.30 | 39.86 | 0.54 | 13.01 | 4.70 | 78.66 | 14.96 | 0.97 |

Comparing the data of Table 1 to Table 2 shows that pretreating the molecular sieve with butene at temperatures the same as or higher than that of the methanol conversion reaction results in a selectivity to ethylene and propylene that is substantially increased relative to catalyst pretreated at lower temperature.

Having now fully described this invention, it will be appreciated by those skilled in the art that the invention can be performed within a wide range of parameters within what is claimed, without departing from the spirit and scope of the invention.

What is claimed is:

1. A process for making an olefin product from an oxygenate feed, the process comprising the steps of:
   a) contacting a metalloaluminophosphate molecular sieve having a porous framework structure with a $C_4$–$C_7$ olefin composition in a pretreatment zone to form an integrated hydrocarbon co-catalyst within the porous framework; and
   b) contacting the metalloaluminophosphate molecular sieve containing the integrated hydrocarbon co-catalyst with an oxygenate in an oxygenate conversion zone to convert the oxygenate to olefin product, wherein the pretreatment zone is at a temperature the same as or higher than that of the reaction zone.

2. The process of claim 1, wherein the pretreatment zone is at a temperature higher than that of the reaction zone.

3. The process of claim 2, wherein the pretreatment zone is at a temperature of at least 10° C. higher than that of the reaction zone.

4. The process of claim 3, wherein the pretreatment zone is at a temperature of at least 20° C. higher than that of the reaction zone.

5. The process of claim 4, wherein the pretreatment zone is at a temperature of at least 50° C. higher than that of the reaction zone.

6. The process of claim 1, wherein the molecular sieve contacting the olefin composition in a pretreatment zone has a carbon content of not greater than 2 wt %, based on total weight of die molecular sieve, prior to contact with the olefin.

7. The process of claim 6, wherein the molecular sieve contacting the olefin composition in a pretreatment zone has a carbon content of not greater than 1.5 wt %, based on total weight of the molecular sieve, prior to contact with the olefin.

8. The process of claim 7, wherein the molecular sieve contacting the olefin composition in a pretreatment zone has a carbon content of not greater than 1 wt %, based on total weight of the molecular sieve, prior to contact with the olefin.

9. The process of claim 8, wherein the molecular sieve contacting the olefin composition in a pretreatment zone has a carbon content of not greater than 0.5 wt %, based on total weight of the molecolar sieve, prior to contact with the olefin.

10. The process of claim 1, wherein the molecular sieve containing the integrated hydrocarbon co-catalyst in the oxygenate conversion zone has a hydrocarbon content of at least 0.1 wt %, based on total weight of the molecular sieve, prior to contacting the oxygenate.

11. The process of claim 10, wherein the molecular sieve containing the integrated hydrocarbon co-catalyst in the oxygenate conversion zone has a hydrocarbon content of at least 1 wt %, based on total weight of the molecular sieve, prior to contacting the oxygenate.

12. The process of claim 11, wherein the molecular sieve containing the integrated hydrocarbon co-catalyst in the oxygenate conversion zone has a hydrocarbon content of at least 5 wt %, based on total weight of the molecular sieve, prior to contacting the oxygenate.

13. The process of claim 1, wherein the molecular sieve of step a) contacts the olefin composition in the pretreatment zone at a WHSV that is lower than that at which the molecular sieve of step b) contacts the oxygenate.

14. The process of claim 13, wherein the molecular sieve of step a) contacts the olefin composition in the pretreatment zone at WHSV that is at least 5 hr$^{-1}$ lower than that at which the molecular sieve of step b) contacts the oxygenate.

15. The process of claim 14, wherein the molecular sieve of step a) contacts the olefin composition in the pretreatment zone at WHSV that is at least 10 hr$^{-1}$ lower than that at which the molecular sieve of step b) contacts the oxygenate.

16. The process of claim 15, wherein the molecular sieve of step a) contacts the olefin composition in the pretreatment zone at WHSV that is at least 15 hr$^{-1}$ lower than that at which the molecular sieve of step b) contacts the oxygenate.

17. The process of claim 1, wherein the molecular sieve of step a) contacts the olefin composition in the pretreatment zone at an olefin to molecular sieve weight ratio of from 0.1:1 to 5:1.

18. The process of claim 17, wherein the molecular sieve of step a) contacts the olefin composition in the pretreatment zone at an olefin to molecular sieve weight ratio of from 0.5:1 to 3:1.

19. The process of claim 18, wherein the molecular sieve of step a) contacts the olefin composition in the pretreatment zone at an olefm to molecular sieve weight ratio of from 1:1 to 2:1.

20. The process of claim 1, wherein the metalloaluminophosphate molecular sieve is silicoaluminophosphate molecular sieve.

21. The process of claim 1, wherein the metallaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, ALPO-11, AlPO-18, ALPO-3 1, ALPO-34, ALPO-36, ALPO-37, ALPO46, metal containing molecular sieves thereof, and combinations thereof.

22. The process of claim 1, wherein the olefin composition contacting the molecular sieve in the pretreatment zone comprises at least 5 wt % olefin, based on total weight of the composition.

23. The process of claim 22, wherein the olefin composition contacting the molecular sieve in the pretreatment zone comprises from 5 wt % to 75 wt % olefin, based on total weight of the composition.

24. The process of claim 23, wherein a majority of the olefin is butene.

25. The process of claim 1, wherein the contact of the molecular sieve of step b) with the oxygenate in the oxygenate conversion zone converts at least 90 wt % of the oxygenate to olefin product.

26. The process of claim 1, wherein at least one olefin in the olefin product is contacted with a polyolefin forming catalyst to form polyolefin.

27. A process for making an olefin product and polyolefin from an oxygenate feed, the process comprising the steps of:
   a) contacting a silicoaluminophosphate molecular sieve with a $C_4$–$C_7$ olefin composition, at an olefin to molecular sieve weight ratio of from 0.1:1 to 5:1, to form an integrated hydrocarbon ca-catalyst within the porous framework;
   b) contacting the silicoaluminophosphate molecular sieve containing the integrated hydrocarbon co-catalyst with an oxygenate to convert the oxygenate to olefin product; and
   c) contacting at least one olefin in the olefin product with a polyolefin forming catalyst to form polyolefin.

28. The process of claim 27, wherein the molecular sieve of step a) contacts the olefin composition at an olefin to molecular sieve weight ratio of from 0.5:1 to 3:1.

29. The process of claim 28, wherein the molecular sieve of step a) contacts the olefin composition at an olefin to molecular sieve weight ratio of from 1:1 to 2:1.

30. The process of claim 27, wherein the contact of the molecular sieve and olefin composition in step a) is at a temperature the same as or higher than that of the contact of the molecular sieve and oxygenate in step b).

31. The process of claim 30, wherein the contact of the molecular sieve and olefin composition in step a) is at a temperature higher than that of the contact of the molecular sieve and oxygenate in step b).

32. The process of claim 31, wherein the contact temperature in step a) is at least 10° C. higher than that the contact temperature in step b).

33. The process of claim 32, wherein the contact temperature in step a) is at least 20° C. higher than that the contact temperature in step b).

34. The process of claim 33, wherein the contact temperature in step a) is at least 50° C. higher than that the contact temperature in step b).

35. The process of claim 27, wherein the molecular sieve contacting the olefin in step a) has a carbon content of not greater than 2 wt %, based on total weight of the molecular sieve, prior to contact with the olefin.

36. The process of claim 35, wherein the molecular sieve contacting the olefin in step a) has a carbon content of not greater than 1.5 wt %, based on total weight of the molecular sieve, prior to contact with the olefin.

37. The process of claim 36, wherein the molecular sieve contacting the olefin in step a) has a carbon content of not greater than 1 wt %, based on total weight of the molecular sieve, prior to contact with the olefin.

38. The process of claim 37, wherein the molecular sieve contacting the olefin in step a) has a carbon content of not greater than 0.5 wt %, based on total weight of the molecular sieve, prior to contact with the olefin.

39. The process of claim 27, wherein the molecular sieve containing the integrated hydrocarbon co-catalyst in step b) has a hydrocarbon content of at least 0.1 wt %, based on total weight of the molecular sieve, prior to contacting the oxygenate.

40. The process of claim 39, wherein the molecular sieve containing the integrated hydrocarbon co-catalyst in step b) has a hydrocarbon content of at least 1 wt %, based on total weight of the molecular sieve, prior to contacting the oxygenate.

41. The process of claim 40, wherein the molecular sieve containing the integrated hydrocarbon co-catalyst in step b) has a hydrocarbon content of at least 5 wt %, based on total weight of the molecular sieve, prior to contacting the oxygenate.

42. The process of claim 41, wherein the molecular sieve of step a) contacts the olefin composition at a WHSV that is lower than that at which the molecular sieve of step b) contacts the oxygenate.

43. The process of claim 27, wherein the molecular sieve of step a) contacts the olefin composition at WHSV that is at least 5 $hr^{-1}$ lower than that at which the molecular sieve of step b) contacts the oxygenate.

44. The process of claim 43, wherein the molecular sieve of step a) contacts the olefin composition at WHSV that is at least 10 $hr^{-1}$ lower than that at which the molecular sieve of step b) contacts the oxygenate.

45. The process of claim 44, wherein the molecular sieve of step a) contacts the olefin composition at WHSV that is at least 15 $hr^{-1}$ lower than that at which the molecular sieve of step b) contacts the oxygenate.

46. The process of claim 27, wherein the silcoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing molecular sieves thereof, and combinations thereof.

47. The process of claim 27, wherein the olefin composition contacting the molecular sieve in step a) comprises at least 5 wt % olefin, based on total weight of the composition.

48. The process of claim 27, wherein the olefin composition contacting the molecular sieve in step a) comprises from 5 wt % to 75 wt % olefin, based on total weight of the composition.

49. The process of claim 48, wherein a majority of the olefin is butene.

50. The process of claim 27, wherein the contact of the molecular sieve with the oxygenate in step b) converts at least 85 wt % of the oxygenate to olefin product.

* * * * *

(12) INTER PARTES REEXAMINATION CERTIFICATE (957th)
United States Patent
Xu et al.

(10) Number: US 7,057,083 C1
(45) Certificate Issued: *Sep. 8, 2014

(54) CATALYST PRETREATMENT WITH C4-C7 OLEFINS IN AN OXYGENATE TO OLEFINS REACTION SYSTEM

(75) Inventors: Teng Xu, Houston, TX (US); Nicolas P. Coute, Houston, TX (US); Kenneth Ray Clem, Humble, TX (US); Keith H. Kuechler, Friendswood, TX (US)

(73) Assignee: ExxonMobill Chemical Patents Inc., Houston, TX (US)

Reexamination Request:
No. 95/001,285, Dec. 18, 2009

Reexamination Certificate for:
Patent No.: 7,057,083
Issued: Jun. 6, 2006
Appl. No.: 10/712,952
Filed: Nov. 12, 2003

(*) Notice: This patent is subject to a terminal disclaimer.

(51) Int. Cl.
*C07C 1/00* (2006.01)
*C07C 1/20* (2006.01)
*C07C 11/08* (2006.01)
*C07C 11/02* (2006.01)
*B01J 29/85* (2006.01)

(52) U.S. Cl.
CPC ............... *C07C 1/20* (2013.01); *C07C 2529/84* (2013.01); *C07C 11/08* (2013.01); *C07C 2529/85* (2013.01); *B01J 29/85* (2013.01); *C07C 11/02* (2013.01)
USPC .......................................... 585/640; 585/639

(58) Field of Classification Search
None
See application file for complete search history.

(56) References Cited

To view the complete listing of prior art documents cited during the proceeding for Reexamination Control Number 95/001,285, please refer to the USPTO's public Patent Application Information Retrieval (PAIR) system under the Display References tab.

*Primary Examiner* — Dwayne Jones

(57) ABSTRACT

This invention relates to processes for converting oxygenates to olefins that include a step of pretreating molecular sieve used in the conversion reaction with a $C_4$-$C_7$ olefin composition, which contains one or more $C_4$-$C_7$ olefins. Fresh or regenerated molecular sieve, which is low in carbon content, is contacted or pretreated with the olefin composition to form a hydrocarbon co-catalyst within the pore structure of the molecular sieve, and the pretreated molecular sieve containing the co-catalyst is used to convert oxygenate to a lighter olefin product.

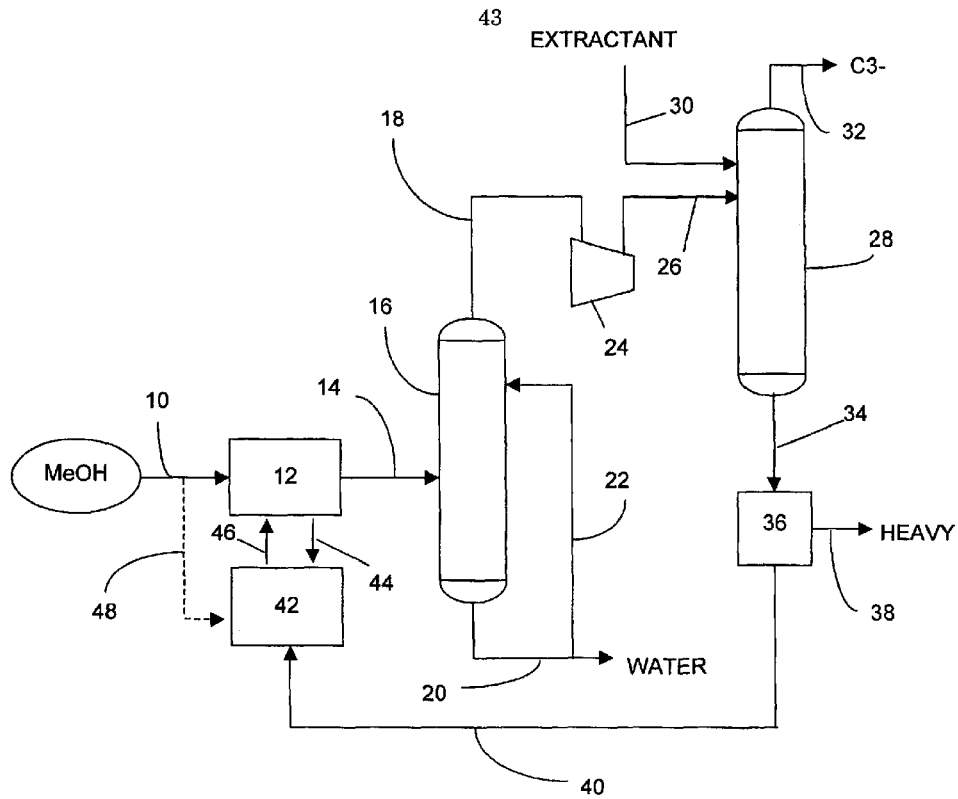

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-50 are cancelled.

\* \* \* \* \*